United States Patent [19]

Melville et al.

[11] Patent Number: 4,863,888

[45] Date of Patent: Sep. 5, 1989

[54] CATALYST CONTAINING COBALT BORON AND OXYGEN AND OPTIONALLY ALUMINUM OF PREPARATION AND PROCESS

[75] Inventors: Judith B. Melville, Downers Grove; L. Charles Hardy, Oak Park; David A. Young, Warrenville, all of Ill.

[73] Assignee: Amoco Corporation, Chicago, Ill.

[21] Appl. No.: 187,836

[22] Filed: Apr. 29, 1988

[51] Int. Cl.[4] .................. B01J 21/02; C01B 35/10; C07C 51/265

[52] U.S. Cl. .................. 502/207; 423/277; 423/279; 502/202; 562/412; 562/413; 562/415; 568/431

[58] Field of Search ............. 502/207, 202; 423/279, 423/277, 283, 286, 593

[56] References Cited

U.S. PATENT DOCUMENTS

| | | | |
|---|---|---|---|
| 1,215,334 | 2/1917 | Bosch et al. | 502/207 |
| 3,644,526 | 2/1972 | Takaki et al. | 502/202 |
| 3,891,707 | 6/1975 | Waddan | 502/207 |
| 4,547,598 | 10/1985 | Sanderson et al. | 502/202 |
| 4,729,979 | 3/1988 | Zletz | 423/279 |
| 4,755,497 | 7/1988 | Simone et al. | 423/279 |

Primary Examiner—Paul E. Konopka
Attorney, Agent, or Firm—Reed F. Riley; William H. Magidson; Ralph C. Medhurst

[57] ABSTRACT

The preparation, structure, and properties of solid inorganic materials containing cobalt, boron, oxygen and, optionally, aluminum, is described. Also described is the use of such materials in catalytic compositions for the conversion of organic compounds. In particular, the new material $Co(BO_2)OH$ is described as well as the use of such material in various catalyzed processes including oxidation of organic compound processes. A particularly useful process is a heterogeneous catalyzed partial oxidation of an alkylaromatic followed by complete oxidation to an aromatic polycarboxlic acid in a water phase.

7 Claims, 1 Drawing Sheet

FIG. 1

CATALYST CONTAINING COBALT BORON AND OXYGEN AND OPTIONALLY ALUMINUM OF PREPARATION AND PROCESS

BACKGROUND OF THE INVENTION

1. Field of the Invention

This invention relates to a crystalline inorganic material containing cobalt, boron and oxygen having a specified X-ray pattern. This invention also relates to a solid inorganic material containing cobalt, boron, oxygen and, optionally, aluminum made by combining sources of cobalt (II) ions, boria and, optionally, alumina in aqueous media within a controlled pH range under autogenous conditions at elevated temperature, and the use of such material in catalytic compositions for the conversion of organic compounds. More particularly, this invention relates to a solid inorganic material containing cobalt, boron and oxygen made by combining sources of cobalt (II) ions and boria in aqueous media within a controlled pH range under autogeneous conditions at elevated temperature, and the use of such solid in catalytic compositions for the conversion of organic compounds, particularly the oxidation and oxidative dehydrogenation of hydrocarbons.

This invention also relates generally to a method for partially oxidizing one or more oxidizable substituents on an aromatic compound and more particularly concerns performance of the aforesaid partial oxidation with the aromatic compound in the liquid phase and in the presence of a solid heterogeneous catalyst to form a partially oxidized aromatic product.

2. Description of the Prior Art

The use of cobalt in catalysts, particularly in the petroleum and petrochemical industries, is well known. Catalysts containing cobalt have been used in the petroleum industry for hydrodesulfurization, hydrodenitrification, and reforming. In the synthetic fuels area, cobaltcontaining catalysts have been used to liquify coal and to upgrade coal, tar sands and shale liquids. The have also been employed as Fischer-Tropsch catalysts. The use of cobalt-containing solids as catalysts is also to be found in the petrochemical industry where they have been used as hydroformylation and polymerization catalysts. Most of these uses in both the petroleum and petrochemical industries employ cobalt-containing catalysts in heterogeneously catalyzed processes. However, these heterogeneous cobalt-containing catalysts are not useful as alkylaromatic oxidation catalysts. An example of the use of a cobalt-containing catalysts system in homogeneous catalysis is in the production of terephthalic acid where paraxylene is oxidized in a liquid-phase process in the presence of oxygen to the aromatic dicarboxylic acid.

In the area of the oxidation of organic materials, both liquid-phase and vapor-phase processes are known For example, phthalic anhydride is made commercially by the vapor-phase oxidation of orthoxylene over a vanadium catalyst and, as described above, terephthalic acid is made by liquid-phase oxidation of terephthalic acid using a cobalt and manganese combination promoted by bromine in acetic acid. Many commercial advantages could result if a stable and active heterogeneous oxidation catalyst could be found for the liquid-phase oxidation of organic compounds, and the importance of such a catalyst would be enhanced if it could also show utility for vapor-phase oxidations.

The published literature also describes a few borate hydroxides. For example, the structures of the minerals szaibelyite, $Mg(BO_2)OH$, and sussexite, $Mn(BO_2)OH$, and mixed Mg/Mn analogues have been published. See J. Mineral, 2,78 (1957). A copper analogue has also been reported. The magnesium compound is described in U.S. Pat. No. 4,160,705 as a coating on electrical steel, and the coating is said to be prepared by electrolytic deposition.

Now it has been found that solid compositions containing cobalt (II), boria, optionally alumina, and oxygen are useful as an oxidation catalyst in a heterogeneously catalyzed liquid-phase process, and that the same compositions also exhibit utility for gas-phase oxidation reactions.

It is well known that aromatic hydrocarbons having at least one oxidizabe substituent group can be converted into carboxylic acid products by effecting oxidation of such groups under controlled conditions. Such conditions have generally included the use of a known oxidation catalyst together with a suitable solvent such as a low molecular weight aliphatic carboxylic acid, such as acetic acid. A typical catalyst system comprises compounds of manganese and/or cobalt, together with a bromine-affording material. U.S. Pat. No. 3,092,658 describes the use of such a process for the continuous oxidation of substituted aromatic hydrocarbons to their corresponding carboxylic acid derivatives, particularly for the preparation of the isomeric phthalic acids from their xylene precursors in an acetic acid solvent.

Such liquid phase oxidation of the oxidizable substituents of an aforesaid aromatic compound to an aromatic carboxylic acid is a highly exothermic chemical reaction. Volatilizable acidic solvents, such as acetic acid, are used both to solubilize the reaction mixture and to dissipate the heat given off by this exothermic reaction. Conventionally, the oxidation in the liquid phase of the oxidizable substituents in the aromatic compound to form aromatic carboxylic acids is generally performed in a vented, well-mixed oxidation reactor, with a substantial portion of the heat generated by the exothermic oxidation reaction being removed by vaporizing directly from the reaction mixture a portion of the solvent and aromatic compound contained within the reactor.

The materials vaporized as a result of the heat generated in the exothermic reaction, together with unreacted oxygen, pass upwardly through the reactor and are withdrawn from the reactor at a point above the reaction mixture liquid level for the reactor. The vapors are passed upwardly and out of the reactor to an overhead reflux condenser system where the vaporized solvent, water and unreacted aforesaid aromatic compound are condensed. The resultant condensate is thereafter separated, e.g., in a reflux splitter, into a portion having a relatively higher water concentration and a portion having a relatively lower water concentration. The separated portion having a relatively lower water concentration, now at a temperature less than the reactor contents' temperature, is refluxed back into the reactor by gravity. Conventionally, the refluxed portion of the condensate is returned directly to the reactor through a process line external to the reactor. The noncondensable gases, carried along with the vaporized reactor material, are vented.

In such an oxidation system the procedures used to recover and dehydrate the solvent are elaborate and expensive and a significant loss of the solvent, typically acetic acid, occurs, and the loss is attributable to oxidation, handling losses, volatility, and the like. In order to avoid this economic penality, attempts have been made to operate without a solvent but without significant success. A more promising approach has involved the use of a solvent system comprising water or some other convenient solvent. However, many of the aforesaid aromatic compounds having oxidizable substituents are only weakly soluble in water or in some of the other likely solvents. Consequently, it is highly desirable to convert in a first stage--for example, by partial oxidation--the aforesaid substituent aromatic compounds to materials that are soluble in water or some other convenient solvent and to do so by a process that permits such materials to be recovered in a highly pure form without the use of costly or elaborate catalyst or solvent separation or treatment procedures. The resulting materials would then be completely oxidized in a second stage in water or some other convenient solvent. Furthermore, even if a low molecular weight carboxylic acid such as acetic acid were employed as the solvent in a second oxidation stage in a multistage oxidation system, it would be highly desirable to employ a first oxidation stage that affords an oxidation product therefrom that also can be recovered in a highly pure form without the use of costly or elaborate catalyst or solvent separation or treatment procedures in the first oxidation stage.

OBJECTS OF THE INVENTION

A general object of the present invention is to produce a new composition useful as a catalyst to convert organic compounds to other compounds.

Another general object of this invention is to produce a new catalyst composition which is useful to oxidize organic compounds and particularly to oxidize alkylaromatic compounds.

A general object of the present invention is to provide an improved method for oxidizing an aromatic compound having at least one oxidizable substituent which solves the aforementioned problems and provides the aforementioned highly desired features.

It is another object of the present invention to provide an improved method for partially oxidizing an aroamtic compound having at least one oxidizable substituent to an intermediate which can be recovered in a highly pure form without the use of costly or elaborate catalyst or solvent separation or treatment procedures.

It is a related object of the present invention to provide an improved method for partially oxidizing an aromatic compound having at least one oxidizable substituent by the use of a solid heterogeneous catalyst.

Other objects and advantages of the invention will become apparent upon reading the following detailed description and appended claims, and upon reference to the accompanying drawings.

SUMMARY OF THE INVENTION

In one aspect, this invention is a crystalline inorganic material containing cobalt, boron and oxygen having an X-ray diffraction pattern containing lines substantially as shown in Table 1.

TABLE 1

| Interplanar Spacing[1] d, Å | Assigned Strength[2] |
|---|---|
| 6.2 ± 0.2 | VS |
| 3.88 ± 0.10 | M |
| 3.35 ± 0.08 | M |
| 3.27 ± 0.08 | M |
| 3.04 ± 0.06 | M |
| 2.67 ± 0.06 | M |
| 2.60 ± 0.06 | M |
| 2.44 ± 0.05 | MS |
| 2.09 ± 0.04 | M |
| 1.94 ± 0.05 | M |

[1] Copper K alpha radiation
[2] VW = very weak; W = weak; M = medium; MS = medium strong; VS = very strong As is generally known, the assigned strengths in X-ray diffraction patterns may vary depending upon the characteristics of the sample. The observed line strength in any particular sample may vary from another sample. Also, X-ray diffraction lines of a particular crystalline material may be obscured by lines from other materials present in a measured sample.

In another aspect, the invention describes the preparation and properties of a solid material containing cobalt, boron and oxygen made by reacting an aqueous mixture having a pH from about 4 to about 9 comprising a source of cobalt (II) ions, and a source of boria, under autogeneous conditions, said solid providing an x-ray pattern containing lines substantially as shown in Table I.

In another aspect, the invention describes the perparation and properties of a solid material having the empirical formula $Co(BO_2)OH$ and providing an x-ray pattern comprising the x-ray diffraction lines and assigned strengths shown in Table I.

Another aspect of the invention is a composition prepared as described above includes a source of alumina to form a solid composition containing cobalt, boron, aluminum and oxygen having an X-ray diffraction pattern containing lines substantially as shown in Table II.

TABLE II

| Interplanar Spacing[1] d, Å | Assigned Strength[2] |
|---|---|
| 6.2 ± 0.2 | M-MS |
| 3.14 ± 0.05 | S-VS |
| 2.67 ± 0.06 | VW-W |
| 2.60 ± 0.06 | VW-W |
| 2.44 ± 0.05 | VW-W |
| 2.34 ± 0.05 | MS |
| 1.84 ± 0.04 | VS |
| 1.76 ± 0.04 | M |
| 1.65 ± 0.03 | M |
| 1.45 ± 0.03 | M |
| 1.43 ± 0.03 | M |
| 1.38 ± 0.02 | W |

[1] Copper K alpha radiation
[2] VW = very weak; W = weak; M = medium; MS = medium strong; VS = very strong In still another aspect, the invention describes the use of such materials in catatyst compositions for the chemical conversion of organic compounds. In a further aspect, the invention describes the use of such materials in the oxidation and partial oxidation of alkylaromatic compounds, and in still a further aspect, the invention describes the use of such materials for the oxidative dehydrogenation of alkanes, cycloalkanes and alkylaromatic compounds.

Another aspect of this invention a method for partially oxidizing an aromatic reactant having at least one phenyl ring or condensed aromatic ring system and substituted with one or more oxidizable substituents typically selected from the group consisting of alkyl, hydroxyalkyl, aldehyde, ketone groups and mixtures thereof, comprising contacting in a first reactor a feed comprising the aforesaid aromatic reactant in the liquid phase with an oxygen-containing gas in the presence of solid heterogeneous catalyst particles preferably at a temperature in the range of from about 50° C. to about 300° C., at a pressure sufficiently high to maintain the aromatic reactant substantially in the liquid phase. In a gas-phase reaction, temperatures may range up to about 1000° C., preferably up to about 600° C..

In a preferred embodiment the method of this invention is also a method to be used in combination with the aforesaid partial oxidation method for substantially completely oxidizing the resulting partially oxidized aromatic product to its corresponding aromatic acid derivative, comprising: oxidizing in a second reactor the partially oxidized, aromatic product dissolved in a solvent at a weight ratio from about 0.20 to about 0.70 parts of the partially oxidized aromatic product per part by weight of solvent in the liquid phase with an oxygen-containing gas at a temperature in the range of from about 100° C. to about 240° C. at a pressure sufficiently high to maintain the solution substantially in the liquid phase, in the presence of an oxidation catalyst comprising a bromine component and at least one catalytic metal component wherein the metal is selected from the group consisting of cobalt, manganese, cerium, iron, nickel, zirconium and mixtures thereof, wherein the weight ratio of bromine (calculated as elemental bromine) in the bromine component-to-total catalytic metals (calculated as the elemental metals) in the catalytic metal component is in the range of from about 0.1 to about 2.5 milligram atoms (mga) per mga of total catalystic metals, and wherein weight ratio of total catalytic metals (calculated as the elemental metals) in the catalytic metal component-to-the parially oxidized aromatic product in the liquid phase oxidation is in the range of from about 4 to about 10 mga per gram mole of the partially oxidized aromatic product.

BRIEF DESCRIPTION OF THE DRAWING

For a more complete understanding of this invention reference should now be made to the embodiment illustrated in greater detail in the accompanying drawing and described below by way of examples of the invention.

In the drawing, THE FIGURE is a schematic illustration of a preferred embodiment of the present invention in which p-xylene is partially oxidized in a distillation column containing a solid heterogeneous catalyst in a first reactor to form partial oxidation products, p-toluic acid and p-tolualdehyde typically which are withdrawn as a highly pure mixture from the bottom of the first reactor and passed to a second reactor where the partial oxidation products, p-toluic acid and p-tolualdehyde, in their aqueous solution are completely oxidized to terephthalic acid in the presence of a catalyst comprising cobalt, manganese and bromine components.

It should be understood that this drawing is only a schematic representation; and, in certain instances, details that are not necessary for an understanding of the present invention or which render other details difficult to perceive may have been omitted. It should be understood, of course, that the invention is not limited to the particular embodiment illustrated herein.

DETAILED DESCRIPTION OF THE INVENTION

The cobalt, boron, optionally aluminum, and oxygen solid materials of this invention can be prepared by crystallizing an aqueous mixture under autogenous conditions, at a controlled pH, of a course of cobalt (II) ions, a source of boria, and optionally, a source of alumina.

The source of cobalt (II) ions can be any reasonably soluble salt of cobalt (II), or precursor thereof, such as the acetate, chloride, bromide, sulfate and the like. Cobalt (II) acetate is preferred. The source of boria is a material such as a borate or boric acid with boric acid being preferred. The source of alumina, if used, is any material capable of producing alumina, but the preferred source is an alumina sol. Typically, best results are obtained when each of the sources used is chosen to reduce the content of foreign anions and cations in the reaction mix.

Typically, the mol ratios of the various reactants can be varied to produce the solid of this invention. Specifically, the mol ratios in terms of oxides of the initial reactant concentrations for $CoO/B_2O_3$ typically are about 0.1 to about 100, preferably about 0.2 to about 80, and most preferably about 0.5 to about 40. If alumina is included in a composition with the cobalt borate identified above, the initial reactant molar ratios in terms of oxides for $Al_2O_3/B_2O_3$ can range up to about 100, preferably about 0.2 to about 80 and more preferably about 0.5 to about 50.

The pH of the reaction mixture is an important variable in the preparation and if the reaction media is too acid or too basic the desired solid typically will not form or other contaminating phases are formed in addition to the desired product. If required, the pH can be adjusted with a base such as ammonia, ethylenediamine, tetramethylammonium hydroxide, sodium hydroxide and the like. Most preferred is the use of ammonium hydroxide.

A typical procedure is to dissolve the boria source and, if desired, the alumina source in water and then add the cobalt (II) ion source. Generally, all components are added with mixing and the resulting slurry is transferred to a closed crystallization vessel for a suitable time. After crystallization, the resulting crystalline product can be filtered, washed with water, and dried.

As described above, too acidic and basic conditions should be avoided during preparation. Advantageously, the pH of the reaction mixture falls within the range of about 4 to about 9; more preferably between about 5 and about 8; and most preferably between about 5 and about 7.

The resulting slurry or solution, if alumina is not used, is transferred to a closed crystallization vessel and reacted usually at a pressure at least the vapor pressure of water for a time sufficient to permit crystallization which usually is about one to about thirty days, typically is about 4 to about 25 days and preferably is about 10 to about 25 days, at a temperature typically above 100° C. and usually ranging from about 100° to about 300° C., preferably about 100° to about 200° C. The crystallizing material can be stirred or agitated as in a rocker bomb. Especially preferred conditions are crystallizing at about 150° C. to about 200° C. for about 10 to about 25 days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° to about 225° C., to form a dry cake which can then be crushed to a powder or to small particles and extruded, pelletized, or made into other forms suitable for its intended use. Prolonged drying times and elevated temperatures may prove detrimental to the crystal structure or may totally destroy it. The aluminum-containing solid thus made generally has a surface area greater than about 30 square meters per gram as measured by the BET procedure. The $Co(BO_2)OH$ can have a surface area to up to about 200 to 300 $m^2/g$.

The alumina-containing cobalt, boron, oxygen materials of the present invention are generally lavender overall in color and show visible evidence of being heterogeneous in that lighter and darker colored components are present. Powder x-ray diffraction shows the total material to be crystalline and contain a substantial proportion of material having the boehmite structure that AlO(OH) exhibits. Contained in the total material is a new phase containing cobalt, boron and oxygen believed to be a cobalt borate with a composition, $Co(BO_2)OH$, which is pinkish also and has an x-ray diffraction pattern containing lines substantially as shown in Table I. This pattern is similar to the X-ray diffraction pattern of the minerals szaibelyite ($Mg(BO_2)OH$) and sussexite ($Mn(BO_2)OH$). This cobalt borate $Co(BO_2)OH$ is monoclinic and has unit cell dimensions: a=10.46; b=12.58 and c=3.09 with $\beta=92.8°$ and $\alpha=\gamma=90°$. As described above, $Co(BO_2)OH$ can be made in the same manner as the cobalt, aluminum, boron, and oxygen material described above by simply eliminating the alumina in the preparation.

The solid materials made by this invention can be admixed with or incorporated within various binders or matrix materials depending upon the intended process use. They are combined with active or inactive materials, synthetic or naturally occurring oxides, as well as inorganic or organic materials which would be useful for binding such substances. Well-known materials include silica, silica-alumina, alumina, magnesia, titania, zirconia, alumina sols, hydrated aluminas, clays such as bentonite or kaolin, or other binders well known in the art.

Catalyst compositions of this invention are useful generally in organic compound, particularly hydrocarbon, conversion reactions. In particular, reactions such as the oxidation of alkyl aromatics and the oxidative dehydrogenation of alkanes, cycloalkanes, and alkylaromatics in either the liquid phase or the vapor phase have been carried out. Useful organic compounds to be oxidized include such materials as alkyl aromatics such as a xylene or t-butylenthylbenzene, an alkane such as hexane or cyclohexane, and like materials. Particularly useful is the fact that when these catalyst compositions are used in liquid-phase oxidation of aromatic hydrocarbons, the active cobalt component is only slowly extracted, leading to longer catalyst lifetime.

Oxidation or oxidative dehydrogenation in the presence of the above-described catalyst compositions is effected by contact of the organic compound either in the liquid or vapor phase at temperatures ranging from about 50° to about 1000° C. Generally, an oxygen-containing gas is used as the oxidant. Air can be used or synthetic mxiture of an inert gas and oxygen made so as to adjust the oxygen level to the desired amount. The reaction takes place at atmospheric pressure, but the pressure may be within the range of about 0 to about 2000 psig. Reaction is suitably accomplished using a weight hourly space velocity of between about 0.01 and about 100. For some compounds reaction in the liquid phase is preferred. Reactions in the liquid phase typically are carried out at about 50° to about 300° C., preferably about 100° to about 260° C. and most preferably at about 100° to about 200° C., with pressures of about 0 to about 300 psig, preferably about 60 to about 250 psig at space velocities from about 0.02 to about 5 $hr^{-1}$, preferably about 0.08 to about 2 $hr^{-1}$. Liquid phase reactions can be carried out in a trickle bed configuration, catalytic distillation configuration or slurry bed configuration, for example. In the gas phase reactions typically are carried out to about 250° to about 1000° C., preferably about 300° to about 600° C. and most preferably at about 400° to about 550° C., with pressures of about 0 to about 300 psig, and space velocities of about 0.01 to about 100 $hr^{-1}$, preferably about 0.5 and about 50 $hr^{-1}$. Gas-phase reactions can be carried out in a fluid bed, stirred bed, fixed bed or other suitable reactor configuration.

In the context of the present invention, 'partial oxidation' means either oxidation of less than all of the oxidizable groups on the aromatic reactant or the oxidation of up to all of the oxidizable groups but not completely to the carboxylic acid derivative.

A suitable feed for use in the partial oxidation method of this invention comprises an aromatic reactant having at least one phenyl ring or a condensed aromatic ring system and substituted with at least one oxidizable substituent selected from the group consisting of alkyl, hydroxyalkyl, alkdehyde, ketone groups and mixtures thereof. Each such alkyl group or the alkyl moiety of each hydroxyalkyl group contains from 1 to 3 carbon atoms and preferably contains one carbon atom. Preferaby each oxidizable substituent is a methyl group. Thus, such typical aromatic reactants include toluene, o-, m-, or p-xylene, pseudocumene, durene, ethylbenzene, o-, m- or p-diethylbenzene, 1,2,4-triethylbenzene, 1,2,4,5-tetraethylbenzene, a propylbenzene, o-, m- or p-dipropylbeznene, 1,2,4-tripropylbenzene, 1,2,4,5-tetrapropylbenzene, a methyl-, ethyl- or propylnaphthalene, a di-(methyl-, or ethyl- or propyl-) naphthalene, 4,4'-dimethylbiphenyl, 4,4-dimethyldiphenyl ether or sulfone, 3,3',4,4'-tetramethylbiphenyl, 3,3',4,4'-tetramethyldiphenyl ether or sulfone, or 3,3',4,4',-tetramethyldiphenylpropane. Preferably the aromatic reactant is p-xylene, psuedocumene, durene, a dimethylnaphthalene, a di-isopropylnaphthalene, or 4,4-dimethyldiphenyl ether or sulfone, 3,3',4,4'-tetramethyldiphenyl ether or sulfone, or 3,3',4,4'-tetramethyldiphenyl propane.

Although the feed can comprise a solvent, such as chlorobenzene, for the aromatic reactant, preferably a solvent is not employed. The aromatic feed comprises preferably at least 80 weight percent, more preferably at least 90 weight percent of the feed. Preferably the feed consists essentially of the aromatic reactant.

Heat generated in the highly exothermic liquid-phase partial oxidation is typically dissipated at least partially by vaporization of unreacted aromatic reactant and, if used, solvent, in the partial oxidation reactor. The resulting vapor and excess oxygen-containing gas are withdrawn from the partial oxidation reactor through a vent above the liquid level in the partial oxidation reactor. The withdrawn aromatic reactant is then condensed in a condenser and recycled to the partial oxidation reactor.

The source of molecular oxygen employed in the oxidation of the method of this invention can vary in molecular oxygen content from that of air to oxygen gas. Air is the preferred source of molecular oxygen. In order to avoid the formation of explosive mixtures, the oxygen-containing gas fed to the partial oxidation reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.0 to 2.8 moles per carbon atom in each oxidizable substituent will provide such 0.5 to 8 volume percent of oxygen (measured on a solvent-free basis) in the gas-vapor mixture in the aforesaid condesner.

The partial oxidation of the method of this invention is performed at a temperature in the range of from about 50° C., preferably from about 100° C., to about 300° C., preferably to about 260° C. The partial oxidation is performed at a pressure which is sufficiently high to maintain the aromatic reactant substantially in the liquid phase. In this context, 'substantially in the liquid phase' means that at least 60 weight percent of the aromatic reactant in the partial oxidation reactor is in the liquid phase. Typically the partial oxidation of the method of this invention is in the range of from about 0, preferably from about 60, to about 300, preferably to about 200 pounds per square inch gauge.

The partial oxidation is performed in the presence of a solid heterogeneous catalyst as described above.

The partial oxidation of the method of this invention can be performed on either a batch or semi-continuous mode. In the batch mode, the aforesaid aromatic reactant, catalyst and, if used, solvent are initially introduced batchwise into the reactor, and the temperature and pressure of the reactor contents are then raised to the desired levels therefor for the commencement of the oxidation reaction. An oxygen-containing gas is introduced continuously into the reactor. After commencement of the oxidation reaction, the temperature of the reactor contents is raised to the desired reaction temperature. In the semi-continuous mode, the catalyst and, if used, solvent are initially introduced batchwise into the reactor, and then the aromatic reactant and air are introduced continuously into the reactor. After commencement of the oxidation reaction, the temperature of the reactor contents is raised to the desired reaction temperature. Preferably, as is described hereinbelow, the semicontinuous mode is employed for the oxidation of the partial oxidation method of this invention.

In each case, the progress of the reaction is monitored by measuring oxygen uptake and temperature changes. A run is terminated after oxygen uptake ceases, as evidenced by a rapid decrease in oxygen uptake--that is, by a rapid incresae in the oxygen concentration in the vapor-gas mixture withdrawn from the reactor.

If the partial oxidation of the method of this invention is performed semicontinuously, the space velocity in the range of from about 0.02, preferably from about 0.08, to about 5, preferably to about 2 parts of the aromatic reactant per part of the catalyst particles by weight per hour is employed. If the partial oxidation of the method of this invention is performed batchwise, the aromatic reactant and catalyst are mixed in a weight ratio in the range of from about 250, preferably from about 1000, to about 10,000, preferably to about 4000 parts of aromatic feed per part of catalyst by weight, and the reaction time is in the range of from about 0.5, preferably from about 1, to about 20, preferably to about 4 hours.

The resulting partially oxidized liquid aromatic product can then be separated from the solid catalyst particles by any convenient solid-liquid separation. The aromatic product can also be separated from any unreacted aromatic reactant by any convenient liquid-liquid separation, such as distillation, by any convenient gas-liquid separation if the unreacted aromatic reactant has been vaporized or by any convenient solid-liquid separation if the temperature is lowered to a point where the partially oxidized aromatic product but not the aromatic reactant crystallizes.

An especially convenient means of both effecting the partial oxidation and separating the partially oxidized, aromatic product from both the catalyst and unreacted aromatic reactant involves catalystic distillation. In such a system, a distillation column in the partial oxidation reactor is packed with a bed of the solid heterogeneous catalyst and is heated to a temperature in the range of suitable reaction temperatures for the partial oxidation. In addition, at least the bottom region of the catalyst bed is maintained at the temperature of at least the boiling point of the aromatic reactant and at least the melting point of the partially oxidized aromatic product but below the boiling point of the partially oxidized, aromatic product, at the pressure employed in the column. Liquid aromatic reactant is introduced into the top of the column and passes downwardly through the column. An oxygen-containing gas is introduced into the bottom of the column and flows upward through the column. The liquid aromatic reactant and oxygen react to form the partially oxidized aromatic product which flows as a liquid downward through the column. Any remaining unreacted aromatic feed continues to flow downward through the column until it vaporizes in the bottom region thereof and then flows upward through the column in the stream of oxygen-containing gas.

Thus, substantially only partially oxidized, aromatic product passes downward out of the column as a liquid and thereby is separated from both the solid catalyst and unreacted aromatic reactant even before it is withdrawn from the partial oxdiation reactor. The resulting aromatic product withdrawn from the partial oxidation reactor is substantially free of unreacted aromatic reactant and contains preferably less than 10 weight percent, more preferably less than 1 weight percent of unreacted aromatic reactant.

In the alternative, a trickle bed catalyst configuration can be employed, in which case both unreacted aromatic reactant and partially oxidized aromatic product pass as a mixture of liquids out of the catalyst bed. In such case, it would be necessary to separate the unreacted aromatic reactant from the partially oxidized aromatic product.

In a preferred embodiment of this invention, the partially oxidized aromatic product produced as described hereinabove is completely oxidized to its carboxylic acid derivative in at least one additional step. Preferably such complete oxidation to the carboxylic acid derivative occurs in a second reactor using a suitable oxidation catalyst and conditions.

The partially oxidized aromatic product of the partial oxidation method of the present invention is soluble in water as well as in other common solvents such as low molecular weight carboxylic acids such as acetic acid. Hence, in a preferred embodiment of the method of this invention, the partially oxidized aromatic product is introduced into a second reactor where it is completely oxidized in the liquid phase by an oxygen-containing gas to its scorresponding carboxylic acid derivative. Hereinafter, water will be used to illustrate the solvent for use in this second oxidation reactor, although other solvents such as acetic acid can be used. Either the partially oxidized product is introduced directly into the second reactor where it dissolves in water already in the second reactor, or the partially oxidized aromatic product is first dissolved in water and the resulting aqueous solution is introduced into the second reactor. In either case, the weight ratio of partially oxidized aromatic product introduced into the second reactor-to-water (or other solvent) is in the range of from about 0.1, preferably from about 0.2, to about 0.4, preferably to about 0.3 parts of the partially oxidized aromatic product per part by weight of water.

Heat generated in the highly exothermic liquid-phase oxidiation in the second reactor is dissipated at least partially by vaporization of the solution in the second reactor. The resulting vapor and excess oxygen-containing gas are withdrawn from the second reactor as a vapor, from which water is then condensed in a condenser and recycled to the second reactor.

The source of molecular oxygen employed in the second oxidation step of the method of this invention can vary in molecular oxygen content from that of air to oxygen gas. Air is the preferred source of molecular oxygen. In order to avoid the formation of explosive mixtures, the oxygen-containing gas fed to the second reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.0 to 2.8 moles per carbon atom in each oxidizable substituent will provide such 0.5 ot 8 volume percent of oxygen (measured on a solvent-free basis) in the gas-vapor mixture in the condenser.

The oxidation in the second reactor is performed at a temperature in the range of from about 100° C., preferably from about 160° C., to about 240° C., preferably to about 210° C., and at a pressure that is sufficiently high to maintain the aqueous solution substantially in the liquid phase. In this context, 'substantially in the liquid phase' means that at least 60 weight percent of the aqueous solution in the second reactor is in the liquid phase. Typically the pressure employed is in the range of from about 100, preferably from about 180, to about 400, preferably to about 220 pounds per square inch gauge.

The catalyst employed in the second reactor comprises preferably a bromine component and at least one catalytic metal component wherein the metal is selected from the group consisting of cobalt, mangansese, cerium, iron, nickel, zirconium and mixtures thereof. The weight ratio of bromine (calculated as elemental bromine) in the bromine component-to-total catalytic metals (calculated as the elemental metals) in the catalytic metal component is in the range of from about 0.1, preferably from about 0.8, to about 2.5, preferably to about 2.0 milligram atoms (mga) of bromine per mga of total catalytic metals. The weight ratio of total catalytic metals (calculated as the elemental metals (in the catalytic metal component-to-the partially oxidized aromatic product in the liquid phase oxidation is in the range from about 4, preferably from about 4.5, to about 10, preferably to about 6 mga per gram mole of the partially oxidized aromatic product.

Preferably the catalyst comprises both cobalt and manganese components, and the atom ratio of manganese-to-cobalt is in the range of from about 0.1, preferably from about 1, to about 4, preferably from about 2 mga of manganese per mga of cobait.

Each of the catalyst components can be provided in any of its known ionic or combined forms that provide soluble forms of bromine and metals, for example, cobalt and managanese, in the solvent in the reactor. For example, when the solvent is an acetic acid medium, cobalt and/or manganese carbonate, acetate tetrahydrate, and/or bromine can be employed. The 0.1 to 2.5 bromine-to-total metal milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetylbromide, tetrabromoethane, ethylene-di-bromide, etc.). The total bromine in molecular bromine and ionic bromide is used to determine satisfaction of the elemental bromine-to-total cobalt and manganese milligram atom ratio of 0.1:1 to 2.5:1. The bromine ion released from the organic bromides at the oxidation operating conditions can be readily determined by known analytical means. Tetrabromoethane, for example, at operating temperatures of 170° to 225° C. has been found to yield about 3 effective gram atoms of bromine per gram mole.

The oxidation in the second reactor in the preferred embodiment of the method of this invention can be performed either on a batch, continuous or semi-continuous mode. In the bath mode, the aforesaid partially oxidized aromatic product, water and catalytic metal and bromine components of the catalyst are initially introduced batchwise into the second reactor, and the temperature and pressure of the reactor contents are then raised to the desired levels therefor for the commencement of the oxidation reaction. Air is introduced continuously into the reactor. After commencement of the oxidation reaction, the temperature of the reactor contents is adjusted to the desired reaction temperature. In the continuous mode, each of the partially oxidized aromatic product, air, water and the catalyst components dissolved in water are continuously introduced into the second reactor where the temperature and pressure are at the desired levels therefor for initiation of the oxidation reaction; and a product stream comprising a slurry of the corresponding carboxylic acid derivative solids in an aqueous solution of catalyst components and possibly some dissolved carboxylic acid derivative is withdrawn from the second reactor. In the semi-continuous mode, the water and the catalyst components are initially introduced batchwise into the reactor, and then the partially oxidized aromatic product and air are introduced continuously into the reactor. After commencement of the oxidation reaction, the temperature of the reactor contents is adjusted to the desired reaction temperature. Preferably, the continuous mode is employed for the second stage or complete oxidation of the method of this invention.

Thereafter, the product stream in the continuous mode or the reactor contents in the batch or semi-continuous mode are cooled to a temperature in the range of from about 10° C. to about 120° C., preferably from about 20° C. to about 32° C., at which temperature the resulting crude, solid acid product is separated by filtration or centrifugation from the product mixture. The use of lower temperatures results in the recovery of a significantly less pure product and the use of higher temperatures results in the recovery of significantly less product. The separated water contains dissolved catalyst components and can then be recycled to the second reactor. The separated acid derivative product is then dried and, if desired or necessary, purified.

Figure 1:
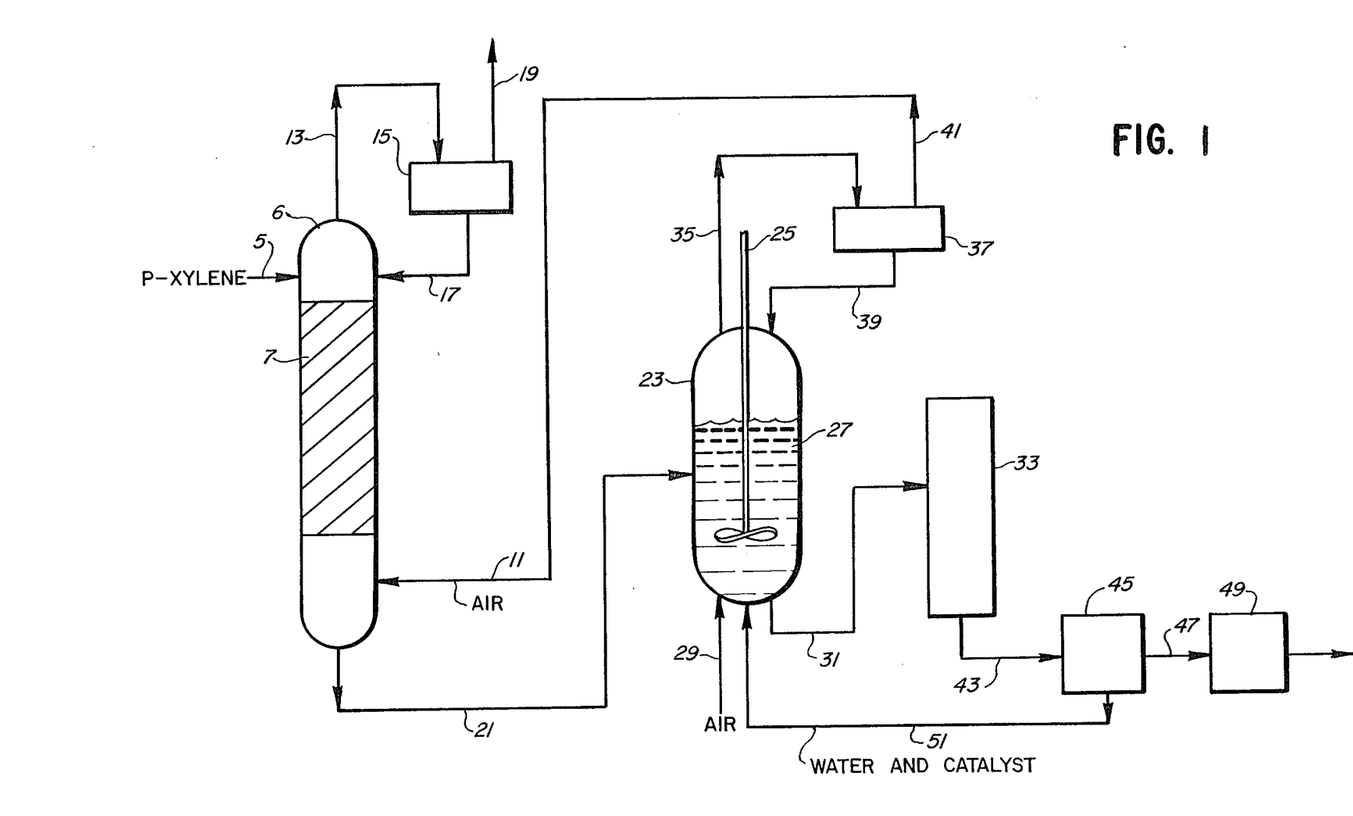

Turning now to THE FIGURE, there is shown a specific and highly preferred embodiment of the method of this invention in which, p-xylene, the aromatic reactant, is introduced through line 5 into the top of a reactor 6 containing a distillation column 7 that is packed with a bed of the solid heterogeneous catalyst particles (not shown). The p-xylene flows downward through the bed of catalyst particles. A stream of air is introduced into the reactor 6 through line 11 and flows upwardly through the catalyst bed therein where it comes into contact with the downwardly moving p-xylene which reacts to form p-toluic acid and p-tolualdehyde.

Unreacted p-xylene is vaporized in the bottom of the distillation column and passes upwardly with the air stream through the distillation column 7, and a mixture of unreacted p-xylene and unreacted air is withdrawn from the top of the reactor 6 and passed in line 13 to a condenser 15 where p-xylene is condensed from the vapor stream and is returned in line 17 to the reactor 6.

The remained uncondensed vapor is substantially air and is vented to the atmosphere through line 19.

An essentially pure mixture of p-toluic acid and p-tolualdehyde is withdrawn from the bottom of the reactor 6 and is passed in line 21 to a second oxidation reactor 23 where it is mixed by mechanical stirrer 25 and dissolved in water to form an aqueous solution 27 of p-toluic acid and p-tolualdehyde. An aqueous solution of a catalyst having cobalt, manganese and bromine components is introduced through line 29 into the reactor 23, where p-toluic acid and p-tolualdehyde are oxidized to terephthalic acid. A product stream comprising a slurry of terephthalic acid solids in an aqueous solution of dissolved catalyst components is withdrawn from the reactor 23 and is passed in line 31 to crystallizer 33.

The exothermic heat from the liquid phase oxidation in reactor 23 is dissipated at least partly by vaporization of the solution 27, and the resulting vapor and unreacted air is vented from the reactor 23 from a point therein above the level of the solution 27 and is passed in line 35 to a condenser 37 where water is condensed and returned in line 39 to the reactor 23. The noncondensible gases are vented in line 41.

The product solution is cooled in the crystallizer 33 whereby terephthalic acid crystallizes, and a slurry of terephthalic acid is withdrawn from the crystallizer 33 in line 43 and passed to a centrifuge 45 where the solid terephthalic acid is separated from the mother liquor and is passed in line 47 to a drier 49 for the final removal of any remaining mother liquor. The mother liquor containing dissolved catalyst components is recycled in line 51 from the centrifuge 45 to the second reactor 23.

The following Examples will serve to illustrate certain specific embodiments of the hereindisclosed invention. These Examples should not, however, be construed as limiting the scope of the novel invention, as there are many variations which may be made thereon without departing from the spirit of the disclosed invention, as those of skill in the art will recognize.

EXAMPLE 1

To a heavy duty mixer was added 1100.89 grams of PHF alumina (American Cyanamid), 107.84 g boric acid and 218 grams cobalt acetate hydrate. The pH after the cobalt acetate addition was 5.18. The increase the pH to 6.44, 49.98 grams of concentrated ammonia was added with mixing. The gel was charged to a 2-liter stainless steel autoclave and was digested with stirring at 177° C. and at autogeneous pressure. After 21 days of digestion, the solid product was filtered and dried at room temperature and 165° C. A 15-gram portion of the dried solid was exchanged with 30 grams of ammonium acetate in 300 grams of distilled water with stirring and heating. The solid product was filtered, washed with distilled water and dried overnight at 165° C. This product was analyzed by powder XRD, ICP elemental analysis and BET surface analysis. Elemental analysis showed 6.8% Co, 36.1% Al and 1.68% B. All percents are weight percents. The BET surface area was determined to be 37 m$^2$/g. The power XRD pattern is set out below:

| Interplanar Spacing d, Å | Assigned Strength |
| --- | --- |
| 6.12 | MS |
| 3.14 | VS |
| 2.65 | VW |
| 2.60 | VW |
| 2.44 | VW |
| 2.34 | MS |
| 1.98 | W |
| 1.84 | VS |
| 1.76 | M |
| 1.65 | M |
| 1.64 | W |
| 1.52 | W |
| 1.45 | M |
| 1.43 | M |
| 1.38 | VW |
| 1.38 | W |

EXAMPLE 2

To a breaker with 800 grams of distilled water was aded 123.66 grams of boric acid and 249.08 grams of cobalt acetate hydrate. The pH of this solution was 4.99 before adding 75.56 grams of ammonium hydroxide to raise the pH to 6.1. This solution was charged to a stainless steel autoclave and digested with stirring at autogeneous pressure and 150° C. for 10 days. The solid product was filtered and dried at room temperature or 150° C. Calculated values for Co(BO$_2$)OH are 49.65 cobalt and 9.1% boron. The XRD powder pattern of the product is set forth below:

| Interplanar Spacing d, Å | Assigned Strength |
| --- | --- |
| 6.27 | VS |
| 5.43 | VW |
| 5.18 | VW |
| 4.62 | VW |
| 3.98 | VW |
| 3.88 | M |

| Interplanar Spacing d, Å | Assigned Strength |
|---|---|
| 3.35 | M |
| 3.27 | M |
| 3.04 | M |
| 3.04 | W |
| 2.67 | M |
| 2.60 | M |
| 2.44 | MS |
| 2.09 | M |
| 1.94 | M |
| 1.85 | VW |
| 1.77 | W |
| 1.73 | W |
| 1.71 | VW |
| 1.55 | VW |
| 1.52 | VW |
| 1.48 | VW |
| 1.44 | VW |
| 1.43 | VW |
| 1.41 | VW |
| 1.40 | VW |
| 1.36 | VW |

EXAMPLE 3

The $Co(BO_2)OH$ portion of the product of Example 1 was isolated either by the Pasteur method or by dispersion of a portion of the Example 1 solid in water. In the water separation method the minor phase $Co(BO_2)OH$ settles to the bottom of the separation vessel and the major amount suspended in the water was decanted. The $Co(BO_2)OH$ material was dried and analyzed yielding 47.0% Co and 8.2% B. Calculated values for $Co(BO_2)OH$ are 49.6% cobalt, 9.1% boron and 40.4% oxygen. The material when examined by infrared spectroscopy showed a medium peak at 3513 cm$^{-1}$ and strong peaks at 1430, 1392, 1267 and 1232 cm$^{-1}$. Thermal gravimetric analysis shows a total weight loss of about 11% by 550° C. with little additional change up to 1000° C. The material was estimated to have a surface area of about 200 m$^2$/g from powder x-ray diffraction data.

The powder XRD pattern of the product is set forth below:

| Interplanar Spacing d, Å | Assigned Strength |
|---|---|
| 8.83 | W |
| 6.29 | VS |
| 5.41 | W |
| 5.21 | M |
| 4.41 | M |
| 3.89 | M |
| 3.35 | M |
| 3.27 | M |
| 3.05 | M |
| 3.01 | W |
| 2.81 | W |
| 2.68 | M |
| 2.65 | VW |
| 2.61 | M |
| 2.45 | MS |
| 2.41 | W |
| 2.33 | M |
| 2.21 | W |
| 2.10 | W |
| 2.04 | VW |
| 2.01 | W |
| 1.99 | W |
| 1.94 | VW |
| 1.77 | W |
| 1.74 | W |
| 1.74 | W |
| 1.73 | VW |

EXAMPLE 4

A 150-gram portion of hydrocarbon was placed in a glass mini-reactor equipped with overhead stirring, an air shaft and condenser. The reactor was adjusted to 400 ml/min flow rate of air (20.9% oxygen), and a 1.00-gram portion of the cobalt-containing solid of Exmaple 1 and the remaining 100 g of hydrocarbon added. The reactor was heated to 120°–140° C. and held constant by means of a Eurotherm controller for a 24–72-hour reaction period. The vent cold trap was linked to an oxygen monitor to observe the progress of oxidation. After reaction was terminated the catalyst was filtered from the mother liquid. A sample of the latter was analyzed to high pressure liquid chromatography to determine the extent of the oxidation, while a second portion of the mother liquor was analyzed by atomic absorption or ICP to determine the extent of cobalt leaching. Table 3 below summarizes the results.

TABLE 3

Conversions, Selectivities, and Catalyst Stability in the Oxidation of Several Hydrocarbons

| | Conversion (wt. %) | Selectivity | Temperature (°C.) | Time (hrs) | Cobalt In Mother Liquor (ppm) |
|---|---|---|---|---|---|
| Paraxylene | 10.8 | (1) | 120 | 24 | 0 |
| Cumene | 3.8 | (2) | 120 | 24 | 1 |
| Pseudocumene | 55 | (3) | 140 | 72 | 0 |
| Orthoxylene | 27 | (4) | 120 | 48 | 0 |

(2) 6.4% toluic acid and 4.2% tolualdehyde
(3) 1.5% acetophenone, 1.4% alpha-methylstyrene, 0.9% benzoic acid
(4) Not determined
(5) 25% o-toluic acid and 2% o-tolualdehyde

EXAMPLE 5

A vycor tube (⅜ inch diameter) was loaded with 18–40 mesh material of Example 1 (3 ml, 1.26 g) and mixed with the same amount of alpha-alumina (1 ml, 0.85 g). After heating the catalyst composition to 100° C., cyclohexane was pumped in at 0.0176 ml/min ($1.63 \times 10^4$ mol/min) and the gas feed switched from nitrogen to 8% $O_2$ in $N_2$ at 110 ml/min ($4.47 \times 10^{-3}$ mols of gas/min) with a WHSV of about 0.66. The molar diluent ratio was 27:1 (gas mixture:cyclohexane). At 400° C., after about 32 hours on stream (with temperature and hydrocarbon shut off after 6 to 7 hour periods) conversion remained at about 31% with selectivities for cyclohexene and benzene of 15% and 79% respectively (based on liquid products).

EXAMPLE 6

A vycor tube (3/8 inch diameter) was loaded with 18–40 mesh of material from Example 1 (3 ml, 1.27 g). After heating to 400° C. cyclopentane was pumped in at 0.0176 ml/min ($1.87 \times 10^{-4}$ mol/min) and gas feed switched from $N_2$ to 8% $O_2$ in $N_2$ at 108 ml/min ($4.38 \times 10^{-3}$ mols of gas/min). The molar diluent ratio was 23:1 (gas mixture:cyclopentane). The products were isolated in a dry ice trap and analyzed by gas chromatography. At 450° C. conversion was about 10% with selectivities of about 79% to cyclopentene and 13% to cyclopentadiene (based on liquid products).

EXAMPLE 7

A 150-gram portion of p-xyelene was placed in a glass three-necked flask equipped with molecular oxygen inlet tube, catalyst tower linked to a condenser, and pressure relief outlet. The apparatus was adjusted to 50 ml/minute flow rate of 6 vol% oxygen in nitrogen and 2.0 grams of aluminum-containing cobalt boron oxides prepared in Example 1 were in the catalyst tower. The reaction was heated to the refluxing temperature of p-xylene (138° C.) for 40 hours reaction period. Upon termination, the mother liquor was found to have 95% p-xylene and 5% undetermined oxidiation products.

What is claimed is:

1. A crystalline material having the chemical composition $Co(BO_2)OH$ and an x-ray diffraction pattern containing lines substantially as described in Table I.
2. A process to make said crystalline material of claim 1 comprising reacting an aqueous mixture having a pH below about 8 comprising a source of Co(II) ions and a source of boria under autogeneous conditions at a temperature above about 100° C.
3. The process of claim 2 wherein the reaction under autogeneous conditions is for about 1 to about 30 days.
4. The process of claim 2 wherein the reaction temperature is about 100° C. to about 300° C.
5. The process of claim 2 wherein the reaction is carried out at a pH of about 4 to about 9.
6. The process of claim 2 wherein the reaction under autogeneous conditions is for about 10 to about 25 days at about 150° C. to about 200° C. at a pH of about 5 to about 7.
7. The crystalline material of claim 1 combined with a binder in an amount sufficient to provide an oxidation catalyst.

* * * * *

UNITED STATES PATENT OFFICE
CERTIFICATE OF CORRECTION

Page 1 of 4

Patent No. 4,863,888　　　　Dated September 5, 1989

Inventor(s) JUDITH B. MELVILLE, L. CHARLES HARDY and DAVID A. YOUNG

It is certified that error appears in the above-identified patent and that said Letters Patent is hereby corrected as shown below:

Title page, Title should read --CATALYST CONTAINING COBALT, BORON AND OXYGEN AND OPTIONALLY ALUMINUM AND PROCESS OF PREPARATION--.

Col. 1, lines 39-40, "cobaltcontaining" should be --cobalt-containing--.

Col. 1, line 41, "The" should be --They--.

Col. 1, line 51, "catalysts" should be --catalyst--.

Col. 3, line 2, "penality" should be --penalty--.

Col. 3, line 44, "aroamtic" should be --aromatic--.

Col. 4, lines 29-30, "perparation" should be --preparation--.

Col. 5, line 14, "embodiment the" should be --embodiment, the--.

Col. 7, line 58, "t-butylenthylbenzene" should be --t-butylethylbenzene--.

Col. 8, line 2, "mxiture" should be --mixture--.

Col. 8, lines 40-41, "Preferaby" should be --Preferably--.

UNITED STATES PATENT OFFICE
CERTIFICATE OF CORRECTION

Patent No. 4,863,888　　　　Dated September 5, 1989

Inventor(s) JUDITH B. MELVILLE, L. CHARLES HARDY and DAVID A. YOUNG

It is certified that error appears in the above-identified patent and that said Letters Patent is hereby corrected as shown below:

Col. 8, line 46, "p-dipropylbeznene" should be --p-dipropylbenzene--.

Col. 8, line 49, "4,4-dimethyldiphenyl" should be --4,4'-dimethyldiphenyl--.

Col. 8, lines 52-53, After "p-xylene," add --m-xylene,--.

Col. 9, lines 18-19, "condesner" should be --condenser--.

Col. 9, line 59, "incresae" should be --increase--.

Col. 9, line 62, "semicontinuously" should be --semi-continuously--.

Col. 10, line 20, "catalystic" should be --catalytic--.

Col. 10, line 47, "oxdiation" should be --oxidation--.

Col. 11, line 7, "scorresponding" should be --corresponding--.

Col. 11, line 23, "oxidiation" should be --oxidation--.

Col. 11, line 58, "mangansese" should be --manganese--.

Col. 12, line 9, "cobait" should be --cobalt--.

Col. 12, line 13, "managanese" should be --manganese--.

Col. 12, line 38, "bath" should be --batch--.

UNITED STATES PATENT OFFICE
CERTIFICATE OF CORRECTION

Patent No. 4,863,888　　　　Dated September 5, 1989

Inventor(s) JUDITH B. MELVILLE, L. CHARLES HARDY and DAVID A. YOUNG

It is certified that error appears in the above-identified patent and that said Letters Patent is hereby corrected as shown below:

| | |
|---|---|
| Col. 13, line 13, | "THE FIGURE," should be --the FIGURE 1,--. |
| Col. 14, line 10, | "The increase the" should be --To increase the--. |
| Col. 14, line 48, | "breaker" should be --beaker--. |
| Col. 14, line 49, | "aded" should be --added--. |
| Col. 14, line 56, | "49.65" should be --49.6%--. |
| Col. 15, lines 29-30, | "Co(BO$_2$-)OH" should be --Co(BO$_2$)OH--. |
| Col. 16, line 23, | "to high" should be --by high--. |
| Col. 16, line 50, | "(1.63 x 10$^4$ mol/min)" should be --(1.63 x 10$^{-4}$ mol/min)--." |

UNITED STATES PATENT OFFICE
CERTIFICATE OF CORRECTION

Patent No. 4,863,888  Dated September 5, 1989

Inventor(s) JUDITH B. MELVILLE, L. CHARLES HARDY and DAVID A. YOUNG

It is certified that error appears in the above-identified patent and that said Letters Patent is hereby corrected as shown below:

Col. 17, line 7, "p-xyelene" should be --p-xylene--.

Col. 18, line 19, "claim 1" should be --claim 2--.

Signed and Sealed this

Twenty-eighth Day of April, 1992

Attest:

HARRY F. MANBECK, JR.

Attesting Officer  Commissioner of Patents and Trademarks